US00PP31958P2

(12) United States Plant Patent
Nishikawa

(10) Patent No.: US PP31,958 P2
(45) Date of Patent: Jul. 7, 2020

(54) ***DELOSPERMA* PLANT NAMED 'P15PY4'**

(50) Latin Name: *Delosperma nubigenum*
Varietal Denomination: P15PY4

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 16/501,799

(22) Filed: Jun. 7, 2019

(30) Foreign Application Priority Data

Apr. 15, 2019 (QZ) ..... PBR 2019/0949

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./422
See application file for complete search history.

*Primary Examiner* — Susan McCormick Ewoldt
(74) *Attorney, Agent, or Firm* — Penny J. Aguirre

(57) ABSTRACT

A new cultivar of *Delosperma* plant named 'P15PY4' that is characterized by its low-growing plant habit, its long blooming period and its flowers with multi-color petals that have creamy white centers, yellow mid-sections and light pastel pink petals.

2 Drawing Sheets

Botanical classification: *Delosperma nubigenum.*
Variety denomination: 'P15PY4'.

CROSS REFERENCE TO RELATED APPLICATIONS

This application is related to U.S. Plant Patents derived from the same breeding program that are entitled *Delosperma* Plant Named 'DE18-162' (U.S. Plant Pat. No. 30,320) and *Delosperma* Plant Named 'WOWDRY1' (U.S. Plant Pat. No. 26,157). This application claims priority to European Community Plant Variety Office (CPVO) Plant Breeder's Rights Application No. 2019/0938 filed on Apr. 12, 2019, the entire contents of which is incorporated by reference herein.

BACKGROUND OF THE INVENTION

The present invention relates to a new and distinct cultivar of *Delosperma* plant, botanically known as *Delosperma nubigenum* 'P15PY4' and will be referred to hereinafter by its cultivar name, 'P15PY4'. The new cultivar of *Delosperma* is an herbaceous perennial grown for container and landscape use.

The new cultivar in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'P15PY4' arose from cross made by the Inventor between unnamed and unpatented proprietary plants of *Delosperma nubigenum* from his breeding program. Seeds were pooled from the crosses and therefore the exact parentage is unknown. 'P15PY4' was selected in May of 2014 as a single unique plant amongst the resulting seedlings.

Asexual propagation of the new cultivar was first accomplished by softwood cuttings in September of 2014 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'P15PY4' as a unique cultivar of *Delosperma.*

1. 'P15PY4' exhibits a low-growing plant habit.
2. 'P15PY4' exhibits a long blooming period.
3. 'P15PY4' exhibits flowers with multi-color petals that have creamy white centers, yellow mid-sections and light pastel pink petals.

'P15PY4' can be most closely compared to *Delosperma cooperi* cultivars 'DE18-162' and 'WOWDRY1'. 'DE18-162' and 'WOWDRY1' are similar to 'P15PY4' is having a low-growing plant habit. 'DE18-162' differs from 'P15PY4' in having flowers that are light pink in color with white centers. 'WOWDRY1' differs from 'P15PY4' in having flowers with petals that are magenta pink on the outer region and yellow and white towards the center of the flower surrounding yellow and white petaloids.

BRIEF DESCRIPTION OF THE DRAWINGS

The accompanying colored photographs illustrate the overall appearance and distinct characteristics of the new *Delosperma*. The photographs were taken of a 2-liter container planted with 5 plants that were 3 months in age as grown in an unheated greenhouse in Noordwijkerhout, The Netherlands.

The photograph in FIG. 1 provides a side view of 'P15PY4' in bloom.

Figure 1:
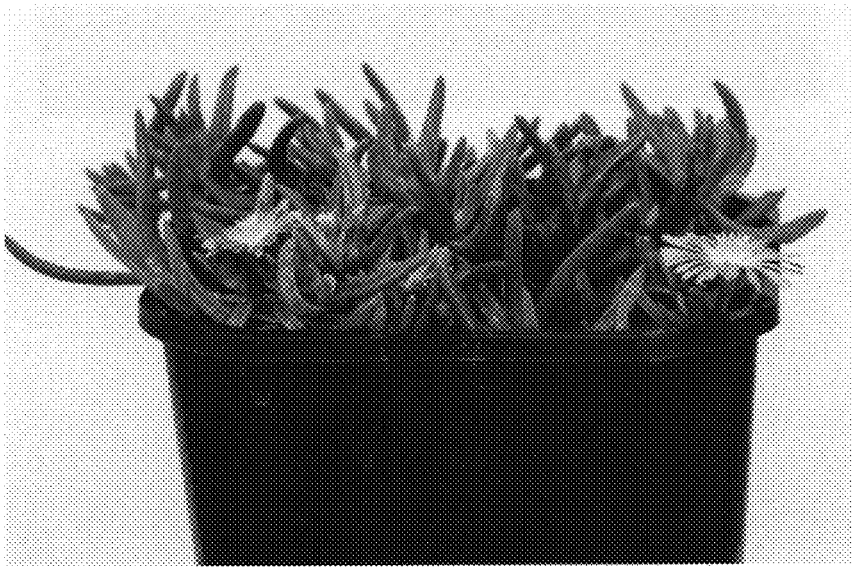
Figure 2:
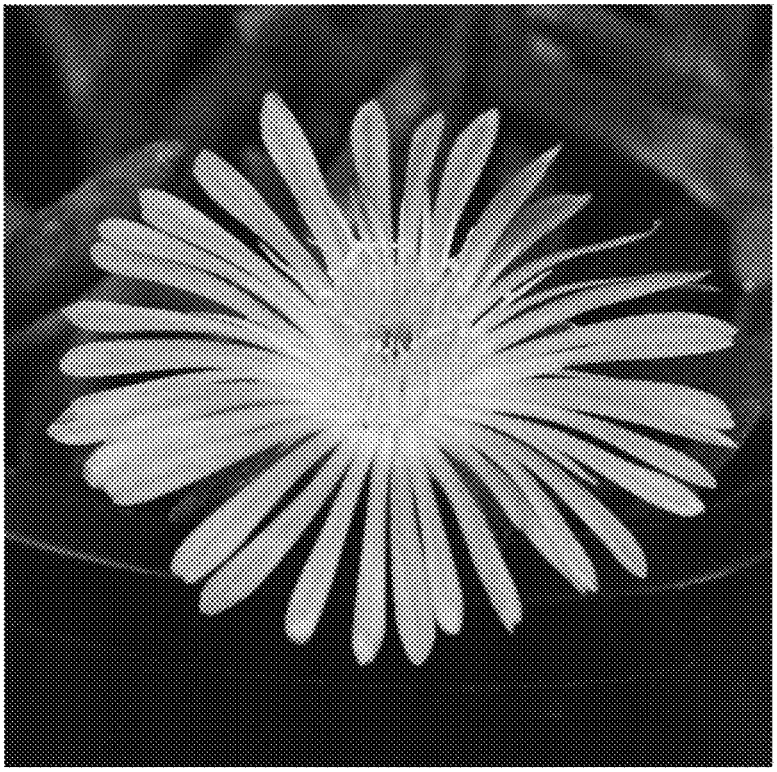

The photograph in FIG. 2 provides a close-up view of a flower of 'P15PY4'.

Figure 3:
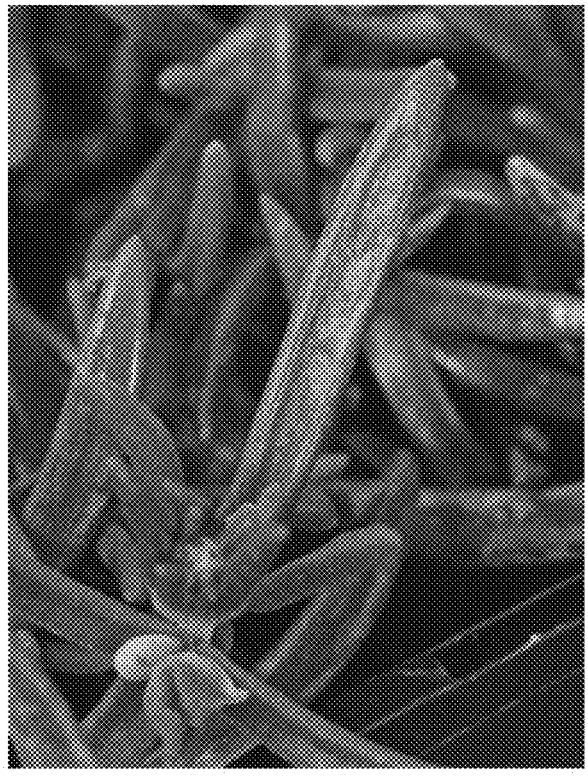

The photograph in FIG. 3 provides a close-up view of the foliage of 'P15PY4'.

The colors in the photographs may differ slightly from the color values cited in the detailed botanical description, which accurately describe the colors of the new *Delosperma*.

DETAILED BOTANICAL DESCRIPTION

The following is a detailed description of 2-liter containers planted with 5 plants that were 3 months in age as grown in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to late summer in Noordwijkerhout, The Netherlands.

*Plant type.*—Herbaceous perennial.

*Plant habit.*—Compact, well-spreading, prostrate.

*Height and spread.*—Reaches about 8.7 cm in height and 12.5 cm in diameter.

*Cold hardiness.*—Observed to be hardy in U.S.D.A. Zones 7 to 12.

*Diseases and pests.*—No susceptibility to resistance to diseases or pests has been observed.

*Root description.*—Fibrous roots, 162D in color.

*Propagation.*—Stem cuttings.

*Growth habit.*—Moderately vigorous.

*Root development.*—Roots initiate and fill a 104-cell plug in 3 weeks and the planted plugs fully develop in 9-cm container within 6 weeks.

Stem description:

*Shape.*—Round.

*Stem color.*—Young stems; upper surface 145A, lower surface 145A to 145B, mature stems; upper surface 177B, lower surface 146D.

*Stem size.*—Lateral branches; an average of 5 cm in length and 3 mm in diameter.

*Internode length.*—An average of 2.2 cm.

*Stem texture.*—Succulent.

*Stem surface.*—Slightly glossy, densely covered with very small glands, average length 0.2 mm, transparent and matching stem surface color.

*Stem aspect.*—Held in multiple angles, average angle of 75°.

*Stem strength.*—Strong.

*Branching habit.*—An average of 4 primary branches and 5 lateral branches per main stem.

Foliage description:

*Leaf shape.*—Ligulate, triangular in cross-section.

*Leaf substance.*—Succulent; an average of 4 mm in thickness.

*Leaf division.*—Simple.

*Leaf base.*—Cuneate.

*Leaf apex.*—Bluntly acute.

*Leaf venation.*—No veins visible.

*Leaf margins.*—Entire.

*Leaf aspect.*—Slightly curved.

*Leaf arrangement.*—Opposite.

*Leaf surface.*—Both surfaces moderately glossy, smooth, densely covered with very small glands, <0.2 mm in length, transparent and matching stem surface color.

*Leaf color.*—Young upper and lower surface; 138B, mature upper surface NN137B, mature lower surface 137B.

*Leaf size.*—About 4.5 cm in length and 5.5 mm in width.

*Leaf quantity.*—Average of 6 (3 pairs) per lateral branch.

*Leaf attachment.*—Sessile.

Inflorescence description:

*Inflorescence type.*—Flowers solitary on terminus and axillary nodes.

*Flower number.*—An average of 9 flowers and 8 buds per plant.

*Flower fragrance.*—Faint, sweet and pleasant.

*Flower aspect.*—Upright to slightly outward.

*Flower longevity.*—Average of 10 days, persistent.

*Flower type.*—Single, rotate.

*Flower size.*—Average of 3.6 cm in height and diameter and 1.1 cm in depth.

*Flower buds.*—Ovate in shape, an average of 9 cm in length and 5 mm in diameter, 138A, base 145A in color, surface is slightly glossy and densely covered with very short glandular hairs an average of 0.2 mm in length, transparent and matching bud surface color.

*Calyx.*—Rotate in shape, average of 8 mm in depth and 2.1 cm in diameter.

*Sepals.*—5, rotate, narrowly ovate to lanceolate in shape, margin entire, an average of 8.5 mm in length and 3 mm in width, bluntly acute apex, broadly cuneate base, color; when opening upper surface NN137B, when opening lower surface 146A, when fully open upper surface 146A, when fully open lower surface NN137B, surfaces; upper and lower surface smooth and densely covered with very small glands average of 0.2 mm in length, transparent and matching surface color, upper surface glossy, lower surface moderately glossy.

*Petals.*—An average of 62 per flower, rotate, average of 2 whorls lower row an average of 42, upper row an average of 20, upper petal row; average of 7 mm in length, 5 mm in width, linear in shape, apex narrow acute, base narrowly cuneate, margin entire, glabrous and velvety surface, color; when opening upper and lower surface 4A to 4B, tips 50A, when fully open upper and lower surface 18D, apex 39B, lower petal row; average of 1.5 cm in length, 2 mm in width, narrow oblanceolate in shape, apex obtuse, base narrowly cuneate, margin entire, glabrous and velvety surface, color; when opening upper and lower surface N66C, changing to 37D at the base, when fully open upper surface N66D, changing to 62A at the base, when fully open lower surface N66D, changing to 63C at the base.

*Petaloids.*—None present.

*Peduncle.*—Average of 1.7 cm in length and 2 mm in diameter, held straight on top of lateral branch at an average of 45°, upper surface color 177A, lower surface color 146D, surface slightly glossy, moderately strong in strength, 145A in color, surface is smooth, moderately glossy and densely covered with very small glands average of 0.2 mm in length, transparent and matching surface color.

*Pedicel.*—None present.

Reproductive organs:

*Pistils.*—Average of 5, style; an average of 1 mm in length and 143A in color, stigma; deltoid in shape, an average of 2 mm in length and 1 mm in diameter, 153B in color, ovary; 147C in color.

*Stamens.*—Average 100, anthers; dorsifixed and oblong in shape, an average of 0.75 mm in length and 0.3 mm in width, 155A in color, filaments; 3 mm in length and 157D in color, pollen; moderate in quantity and 12B to 12C in color.

*Fruit/seed.*—Fruit and seed production has not been observed to date.

It is claimed:

1. A new and distinct variety of *Delosperma* plant named 'P15PY4' as described and illustrated herein.

* * * * *